United States Patent
Sun et al.

(10) Patent No.: US 12,274,710 B2
(45) Date of Patent: Apr. 15, 2025

(54) COMPOUND FOR REGULATING BODY WEIGHT IMBALANCE, COMPOSITION THEREOF AND APPLICATION THEREOF

(71) Applicants: GUANGZHOU CENTURY CLINICAL RESEARCH CO., LTD, Guangzhou (CN); GUANGZHOU XIN-CHUANGYI BIOPHARMACEUTICAL CO., LTD, Guangzhou (CN); XIANGBEI WELMAN PHARMACEUTICAL CO., LTD, Hunan (CN); GUANGZHOU WELMAN NEW DRUG R&D CO., LTD., Guangzhou (CN); NANJING KANGFUSHUN PHARMACEUTICAL CO., LTD, Jiangsu (CN)

(72) Inventors: Tianyu Sun, Guangzhou (CN); Mingjie Sun, Guangzhou (CN); Guixing Deng, Guangzhou (CN); Changqing Li, Guangzhou (CN)

(73) Assignees: GUANGZHOU CENTURY CLINICAL RESEARCH CO., LTD, Guangzhou (CN); GUANGZHOU XIN-CHUANGYI BIOPHARMACEUTICAL CO., LTD, Guangzhou (CN); XIANGBEI WELMAN PHARMACEUTICAL CO., LTD, Hunan (CN); GUANGZHOU WELMAN NEW DRUG R & DCO., LTD., Guangzhou (CN)

( * ) Notice: Subject to any disclaimer, the term of this patent is extended or adjusted under 35 U.S.C. 154(b) by 749 days.

(21) Appl. No.: 17/608,203

(22) PCT Filed: Apr. 24, 2020

(86) PCT No.: PCT/CN2020/086698
§ 371 (c)(1),
(2) Date: Nov. 2, 2021

(87) PCT Pub. No.: WO2020/224452
PCT Pub. Date: Nov. 12, 2020

(65) Prior Publication Data
US 2022/0193104 A1 Jun. 23, 2022

(30) Foreign Application Priority Data
May 5, 2019 (CN) .................. 201910365916.X

(51) Int. Cl.
*A61K 31/7048* (2006.01)
*A61P 3/04* (2006.01)

(52) U.S. Cl.
CPC ............ *A61K 31/7048* (2013.01); *A61P 3/04* (2018.01)

(58) Field of Classification Search
None
See application file for complete search history.

(56) References Cited

U.S. PATENT DOCUMENTS

| 5,296,469 A | * 3/1994 | Orjales-Venero ......... A61P 1/04 514/928 |
| 6,110,891 A | 8/2000 | Pusztai et al. |

FOREIGN PATENT DOCUMENTS

| CN | 1692909 A | 11/2005 | |
| CN | 108992456 A | 12/2018 | |
| WO | WO-2004054570 A1 | * 7/2004 | ........... A61K 31/137 |

OTHER PUBLICATIONS

International Search Report dated Jul. 23, 2020 issued in corresponding PCT/CN2020/086698 application (3 pages).
English Translation of Written Opinion of the International Search Authority dated Jul. 23, 2020 issued in corresponding PCT/CN2020/086698 application (2 pages).
V.M. Nakajima et al., "Citrus Bioactive Phenolics: Role in the Obesity Treatment", LWT—Food Science and Technology, vol. 59 (2014) pp. 1205-1212.
I. Villegas et al., "A New Flavonoid Derivative, Dosmalfate, Attenuates the Development of Dextran Sulphate Sodium-Induced Colitis in Mice", International Immunopharmacology, vol. 3 (2003) pp. 1731-1741.
C.C. Hsu et al., "Diosmin, A Citrus Nutrient, Activates Imidazoline Receptors to Alleviate Blood Glucose and Lipids in Type 1-Like Diabetic Rats", Nutrients, vol. 9 (2017) pp. 1-11.
First Office Action in Chinese Application No. 2020800020530, dated Mar. 19, 2023 (4 pages) with an English translation.
First Search Report for Chinese Application No. 2020800020530, dated Apr. 24, 2020 (2 pages) with an English translation.
Second Office Action in Chinese Application No. 2020800020530, dated Jul. 27, 2023 (3 pages) with an English translation.
Third Office Action in Chinese Application No. 2020800020530, dated Oct. 10, 2023 (3 pages) with an English translation.
Extended European search report of family patent EP20802344, dated May 18, 2022.

* cited by examiner

*Primary Examiner* — Dale R Miller
(74) *Attorney, Agent, or Firm* — Millen, White, Zelano & Branigan, PC; Ryan Pool

(57) ABSTRACT

A compound for regulating body weight imbalance, a composition thereof and an application thereof. The inventor unexpectedly discovered that diosmin hydrogen sulfate derivatives have the effects of regulating body weight imbalance, and are expected to be developed as safe and effective weight imbalance regulators or used as synergists to improve the regulatory effects of existing weight imbalance regulators.

15 Claims, No Drawings

COMPOUND FOR REGULATING BODY WEIGHT IMBALANCE, COMPOSITION THEREOF AND APPLICATION THEREOF

CROSS-REFERENCE TO RELATED APPLICATIONS

The present application is a national phase entry under 35 USC § 371 of International Application PCT/CN2020/086698, filed on Apr. 24, 2020, which claims the benefit of and priority to Chinese Patent Application No. 201910365916X, filed on May 5, 2019, the entire disclosures of which are incorporated herein by reference.

TECHNICAL FIELD

The present disclosure relates to a new use of a compound, in particular to a new use of a diosmin hydrogen sulfate derivative, especially the use in regulating body weight imbalance.

BACKGROUND

Based on the normal metabolism of human body, a body weight balance can be maintained within a certain range. Overweight and underweight are both sub-healthy or belong to pathological state. There are many factors causing the body weight imbalance, such as genetic factors, insufficient physical exercise, insufficient or excessive intake of nutrients, disease, drug use, etc.

At present, obesity and overweight have become a global health problem. The obesity can cause a variety of diseases. The probability that obese people suffer from diabetes is more than 4 times that of normal people. The proportion of obese persons suffering from hypertension is 20%-50%, which is obviously higher than that of normal people, and the chance of obese people to suffer from cardiovascular and cerebrovascular diseases such as myocardial infarction, stroke and the like is obviously higher than that of normal people. Obesity also causes more malignant tumors as well as gout, disorders of menstruation, sleep apnea, and many other diseases. Obesity is not only a predisposing factor of diseases but also closely related to the prognosis of the diseases. For example, when the weight of a patient suffering from diabetes is controlled, the blood glucose level can be controlled better. Obesity and related diseases thereof have seriously affected people's health and quality of life.

Reducing weight can effectively improve health of patients who are suffering from obesity-related diseases and complications. Lifestyle interventions led by diet and exercise are recommended. However, for many people, it is very difficult to change lifestyle, and these measures are not always effective. Drug administration is one of necessary options for reducing weight. If body weight is reduced by 5% or more within 3 months after drug administration, it is recommended to continue the drug administration, which is described in the Pharmacological Management of Obesity: An Endocrine Society Clinical Practice Guideline.

However, currently in Europe and China, orlistat is only one type of anti-obesity drugs approved by the drug administration. The types of anti-obesity drugs approved by the US Food and Drug Administration (FDA) are also very limited and there are many adverse reactions. Phentermine and its similar drugs can be used for significantly reducing body weight by promoting release of norepinephrine, but many adverse reactions such as increased blood pressure, palpitations, tachycardia, and myocardial ischemia are observed, which severely restrict their application in patients suffering from cardiovascular diseases. Lorcaserin is a selective serotonin receptor (5-HT2C) agonist and can suppress appetite and reduce weight, but its risks of cardiovascular diseases, heart valve diseases and carcinogenicity still need to be further confirmed in long-term use. As a pancreatic and gastric lipase inhibitor, orlistat reduces weight by reducing fat absorption, but has a limited weight reduction effect, and may cause indigestion of fat, absorption disorders of vitamins and minerals and other adverse reactions. As a glucagon-like peptide-1 (GLP-1) receptor agonist, liraglutide reduces weight by adjusting food and calorie intake, but requires injections, which affects patient compliance. Some drugs for treating other diseases also can assist in reducing weight, such as hypoglycemic drugs (e.g. metformin and an SGLT2 inhibitor), and anti-epileptic drugs (e.g. zonisamide, topiramate), but the efficacy is limited. At present, there is still a huge clinical demand for new anti-obesity drugs.

SUMMARY

The objective of the present disclosure is to provide a new use of a diosmin hydrogen sulfate derivative. In order to achieve the above objective, the present disclosure relates to the following technical solutions.

The technical solution in the first aspect of the present disclosure is:

A use of a compound in preparing a weight imbalance regulator, wherein the compound is at least one selected from the group consisting of a hydrogen sulfate having a general structure of formula (I), a metal salt of the hydrogen sulfate having the general structure of formula (I), and a metal complex of the hydrogen sulfate having the general structure of formula (I):

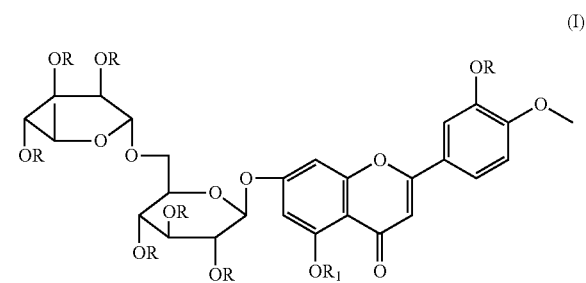

in formula (I),
each R is independently selected from H or $-SO_3H$, $R_1$ is selected from H or $-SO_3H$, and R and $R_1$ are not both H; and preferably, R is $-SO_3H$.

In some embodiments of the use of a compound in preparing a weight imbalance regulator, the compound is selected from a metal salt or a metal complex of the hydrogen sulfate having the general structure of formula (I).

In some embodiments of the use of a compound in preparing a weight imbalance regulator, the metal is selected from sodium, potassium, calcium, aluminum or magnesium.

In some embodiments of the use of a compound in preparing a weight imbalance regulator, the compound is a metal complex formed by combining the hydrogen sulfate having the general structure of formula (I) and a metal hydroxide.

In some embodiments of the use of a compound in preparing a weight imbalance regulator, the compound is selected from a sodium salt, a potassium salt, an aluminum complex, a magnesium complex or a magnesium-aluminum complex of the hydrogen sulfate having the general structure of formula (I).

In some embodiments of the use of a compound in preparing a weight imbalance regulator, the compound has a structure of formula (II):

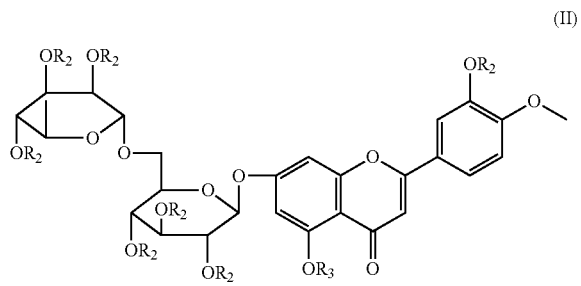

(II)

in formula (II),
$R_2$ is $SO_3Na$ and $R_3$ is H; or
$R_2$ is $SO_3Na$ and $R_3$ is $SO_3Na$; or
$R_2$ is $SO_3[Al_2(OH)_5]$ and $R_3$ is H; or
$R_2$ is $SO_3[Al_2(OH)_5]$ and $R_3$ is $SO_3[Al_2(OH)_5]$.

In some embodiments of the use of a compound in preparing a weight imbalance regulator, the weight imbalance regulator is an oral preparation, which is more conducive to taking.

In some embodiments of the use of a compound in preparing a weight imbalance regulator, the weight imbalance indicates that the BMI index is not less than 24, or not less than 25, 26, 27 or 28.

The technical solution in the second aspect of the present disclosure is:

A use of a compound in preparing a synergist of a weight imbalance regulator, wherein the compound is at least one selected from the group consisting of a hydrogen sulfate having a general structure of formula (I), a metal salt of the hydrogen sulfate having the general structure of formula (I), and a metal complex of the hydrogen sulfate having the general structure of formula (I):

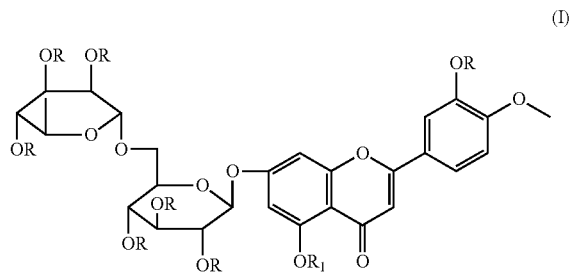

(I)

in formula (I),
each R is independently selected from H or —$SO_3H$, $R_1$ is selected from H or —$SO_3H$, and R and $R_1$ are not both H; and preferably, R is —$SO_3H$.

In some embodiments of the use of a compound in preparing a synergist of a weight imbalance regulator, the compound is selected from a metal salt or a metal complex of the hydrogen sulfate having the general structure of formula (I).

In some embodiments of the use of a compound in preparing a synergist of a weight imbalance regulator, the metal is selected from sodium, potassium, calcium, aluminum or magnesium.

In some embodiments of the use of a compound in preparing a synergist of a weight imbalance regulator, the compound is a metal complex formed by combining the hydrogen sulfate having the general structure of formula (I) and a metal hydroxide.

In some embodiments of the use of a compound in preparing a synergist of a weight imbalance regulator, the compound is selected from a sodium salt, a potassium salt, an aluminum complex, a magnesium complex or a magnesium-aluminum complex of the hydrogen sulfate having the general structure of formula (I).

In some embodiments of the use of a compound in preparing a synergist of a weight imbalance regulator, the compound has a structure of formula (II):

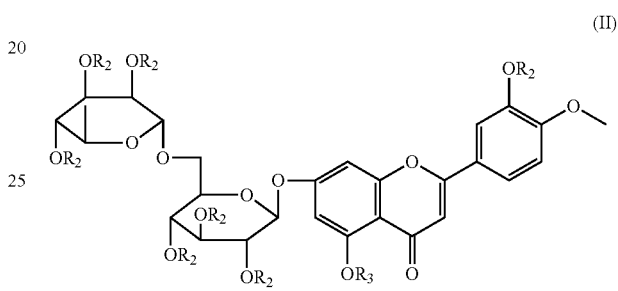

(II)

in formula (II),
$R_2$ is $SO_3Na$ and $R_3$ is H; or
$R_2$ is $SO_3Na$ and $R_3$ is $SO_3Na$; or
$R_2$ is $SO_3[Al_2(OH)_5]$ and $R_3$ is H; or
$R_2$ is $SO_3[Al_2(OH)_5]$ and $R_3$ is $SO_3[Al_2(OH)_5]$.

In some embodiments of the use of a compound in preparing a synergist of a weight imbalance regulator, the weight imbalance regulator is at least one selected from the group consisting of norepinephrine promoters, selective serotonin receptor agonists, lipase inhibitors, and glucagon-like peptide-1 receptor agonists. Through combined use, it is expected to further improve the efficacy of existing weight imbalance regulators or to reduce the side effects.

In some embodiments of the use of a compound in preparing a synergist of a weight imbalance regulator, the weight imbalance regulator is at least one selected from the group consisting of phentermine, bupropion, lorcaserin, orlistat, cetilistat, liraglutide, metformin, zonisamide, topiramate, naltrexone, AMG-598, amitifadine, tesofensine, RZL-12, and other known weight imbalance regulators or compounds having a function of regulating weight imbalance.

The technical solution in the third aspect of the present disclosure is:

A compound for preparing a weight imbalance regulator or a synergist of a weight imbalance regulator, wherein the compound is at least one selected from the group consisting of a hydrogen sulfate having a general structure of formula (I), a metal salt of the hydrogen sulfate having the general structure of formula (I), and a metal complex of the hydrogen sulfate having the general structure of formula (I):

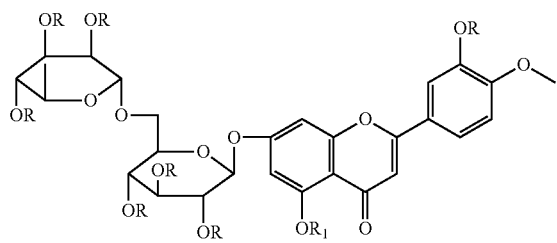

(I)

in formula (I), each R is independently selected from H or —SO$_3$H, R$_1$ is selected from H or —SO$_3$H, and R and R$_1$ are not both H; and preferably, R is —SO$_3$H.

In some embodiments of a compound for preparing a weight imbalance regulator or a synergist of a weight imbalance regulator, the compound is selected from a metal salt or a metal complex of the hydrogen sulfate having the general structure of formula (I).

In some embodiments of a compound for preparing a weight imbalance regulator or a synergist of a weight imbalance regulator, the metal is selected from sodium, potassium, calcium, aluminum or magnesium.

In some embodiments of a compound for preparing a weight imbalance regulator or a synergist of a weight imbalance regulator, the compound is a metal complex formed by combining the hydrogen sulfate having the general structure of formula (I) and a metal hydroxide.

In some embodiments of a compound for preparing a weight imbalance regulator or a synergist of a weight imbalance regulator, the compound is selected from a sodium salt, a potassium salt, an aluminum complex, a magnesium complex or a magnesium-aluminum complex of the hydrogen sulfate having the general structure of formula (I).

In some embodiments of a compound for preparing a weight imbalance regulator or a synergist of a weight imbalance regulator, the compound has a structure of formula (II):

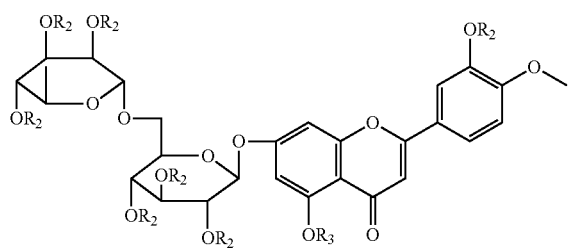

(II)

in formula (II),

R$_2$ is SO$_3$Na and R$_3$ is H; or
R$_2$ is SO$_3$Na and R$_3$ is SO$_3$Na; or
R$_2$ is SO$_3$[Al$_2$(OH)$_5$] and R$_3$ is H; or
R$_2$ is SO$_3$[Al$_2$(OH)$_5$] and R$_3$ is SO$_3$[Al$_2$(OH)$_5$].

In some embodiments of a compound for preparing a weight imbalance regulator or a synergist of a weight imbalance regulator, weight imbalance indicates that the BMI index is not less than 24, or not less than 25, 26, 27 or 28.

In some embodiments of a compound for preparing a weight imbalance regulator or a synergist of a weight imbalance regulator, the weight imbalance regulator in the "synergist of a weight imbalance regulator" is at least one selected from the group consisting of norepinephrine promoters, selective serotonin receptor agonists, lipase inhibitors, and glucagon-like peptide-1 receptor agonists. Through combined use, it is expected to further improve the efficacy of existing weight imbalance regulators or to reduce the side effects.

In some embodiments of a compound for preparing a weight imbalance regulator or a synergist of a weight imbalance regulator, the weight imbalance regulator in the "synergist of a weight imbalance regulator" is at least one selected from the group consisting of phentermine, bupropion, lorcaserin, orlistat, cetilistat, liraglutide, metformin, zonisamide, topiramate, naltrexone, AMG-598, amitifadine, tesofensine, RZL-12, and other known weight imbalance regulators or compounds having a function of regulating weight imbalance.

The technical solution in the fourth aspect of the present disclosure is:

A method of regulating weight imbalance, comprising orally administering an effective amount of a compound to people with weight imbalance, wherein the compound is at least one selected from the group consisting of a hydrogen sulfate having a general structure of formula (I), a metal salt of the hydrogen sulfate having the general structure of formula (I), and a metal complex of the hydrogen sulfate having the general structure of formula (I):

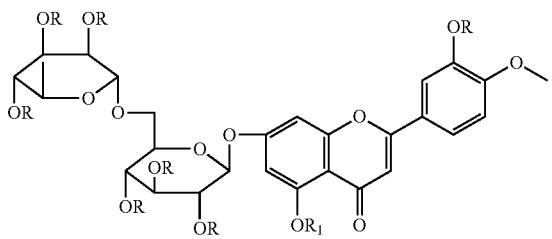

(I)

in formula (I), each R is independently selected from H or —SO$_3$H, R$_1$ is selected from H or —SO$_3$H, and R and R$_1$ are not both H; and preferably, R is —SO$_3$H.

In some embodiments of regulating weight imbalance, the compound is selected from a metal salt or a metal complex of the hydrogen sulfate having the general structure of formula (I).

In some embodiments of regulating weight imbalance, the metal is selected from sodium, potassium, calcium, aluminum or magnesium.

In some embodiments, the compound is a metal complex formed by combining the hydrogen sulfate having the general structure of formula (I) and a metal hydroxide.

In some embodiments of regulating weight imbalance, the compound is selected from a sodium salt, a potassium salt, an aluminum complex, a magnesium complex or a magnesium-aluminum complex of the hydrogen sulfate having the general structure of formula (I).

In some embodiments of regulating weight imbalance, the compound has a structure of formula (II):

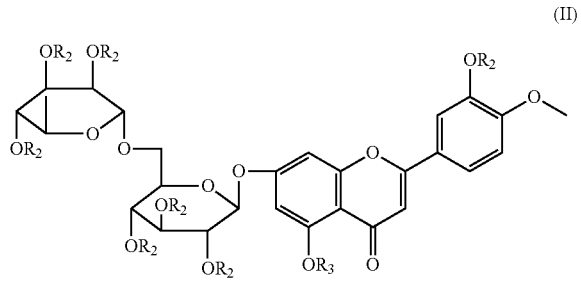

in formula (II),
R$_2$ is SO$_3$Na and R$_3$ is H; or
R$_2$ is SO$_3$Na and R$_3$ is SO$_3$Na; or
R$_2$ is SO$_3$[Al$_2$(OH)$_5$] and R$_3$ is H; or
R$_2$ is SO$_3$[Al$_2$(OH)$_5$] and R$_3$ is SO$_3$[Al$_2$(OH)$_5$].

In some embodiments of regulating weight imbalance, the weight imbalance indicates that the BMI index is not less than 24, or not less than 25, 26, 27 or 28.

In some embodiments of regulating weight imbalance, the method further comprises administering other weight imbalance regulators. That is, in addition to administering the compound, the method may also comprise administering other substances applicable for regulating weight imbalance.

In some embodiments of regulating weight imbalance, the other weight imbalance regulators are at least one selected from the group consisting of norepinephrine promoters, selective serotonin receptor agonists, lipase inhibitors, and glucagon-like peptide-1 receptor agonists. By drug combination of the compound and other weight imbalance regulators or preparing a compound preparation, it is expected to further improve the efficacy of existing weight imbalance regulators or to reduce the side effects.

In some embodiments of regulating weight imbalance, the other weight imbalance regulators are at least one selected from the group consisting of phentermine, bupropion, lorcaserin, orlistat, cetilistat, liraglutide, metformin, zonisamide, topiramate, naltrexone, AMG-598, amitifadine, tesofensine, RZL-12, and other known weight imbalance regulators or compounds having a function of regulating weight imbalance.

In some embodiments of regulating weight imbalance, the oral dose of the compound is 0.05 g-50 g/day, 0.1 g-30 g/day, 0.5 g-20 g/day, 1 g-18 g/day or 1 g-9 g/day.

In some embodiments of regulating weight imbalance, the compound is administrated orally 1-3 times/day.

In some embodiments of regulating weight imbalance, the method is for therapeutic or non-therapeutic purposes, and the non-therapeutic purposes may be preventive purposes or health-care purposes.

In some embodiments of regulating weight imbalance, through implementing the method, the extent of weight imbalance can be reduced.

In some embodiments of regulating weight imbalance, through implementing the method, the BMI value of a person suffering from weight imbalance can be closer to a normal range.

In some embodiments of regulating weight imbalance, a person suffering from weight imbalance has a BMI index of not less than 24, or not less than 25, 26, 27 and 28; and through implementing the method, the BMI index of the person suffering from weight imbalance can be reduced.

In some embodiments of regulating weight imbalance, no damage to the digestive function of the person suffering from weight imbalance is caused by the method.

The technical solution in the fifth aspect of the present disclosure is:

A composition for regulating weight imbalance, comprising an active ingredient, wherein the active ingredient comprises at least one selected from the group consisting of a hydrogen sulfate having a general structure of formula (I), a metal salt of the hydrogen sulfate having a general structure of formula (I), and a metal complex of the hydrogen sulfate having a general structure of formula (I):

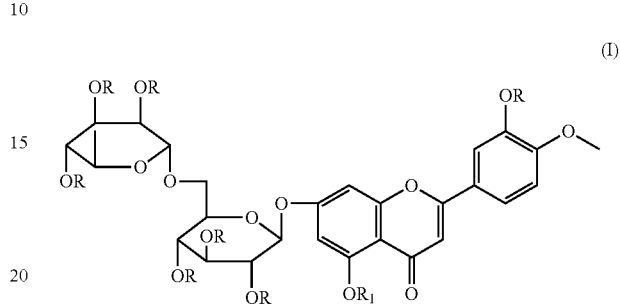

in formula (I),
each R is independently selected from H or —SO$_3$H, R$_1$ is selected from H or —SO$_3$H, and R and R$_1$ are not both H; and preferably, R is —SO$_3$H.

In some embodiments of a composition for regulating weight imbalance, the active ingredient comprises a metal salt or a metal complex of a hydrogen sulfate having the general structure of formula (I).

In some embodiments of a composition for regulating weight imbalance, the metal is selected from sodium, potassium, calcium, aluminum or magnesium.

In some embodiments of a composition for regulating weight imbalance, the active ingredient comprises a metal complex formed by combining the hydrogen sulfate having the general structure of formula (I) and a metal hydroxide.

In some embodiments of a composition for regulating weight imbalance, the active ingredient comprises a sodium salt, a potassium salt, an aluminum complex, a magnesium complex or a magnesium-aluminum complex of the hydrogen sulfate having the general structure of formula (I).

In some embodiments of a composition for regulating weight imbalance, the active ingredient comprises a compound having a structure of formula (II):

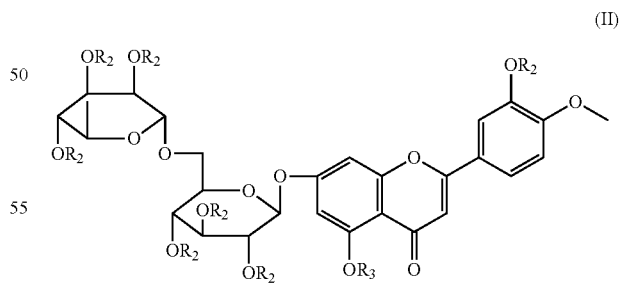

in formula (II),
R$_2$ is SO$_3$Na and R$_3$ is H; or
R$_2$ is SO$_3$Na and R$_3$ is SO$_3$Na; or
R$_2$ is SO$_3$[Al$_2$(OH)$_5$] and R$_3$ is H; or
R$_2$ is SO$_3$[Al$_2$(OH)$_5$] and R$_3$ is SO$_3$[Al$_2$(OH)$_5$].

In some embodiments of a composition for regulating weight imbalance, the composition also comprises at least one pharmaceutically acceptable excipient.

In some embodiments of a composition for regulating weight imbalance, the composition also comprises at least one of other weight imbalance regulators.

In some embodiments of a composition for regulating weight imbalance, the other weight imbalance regulators are at least one selected from the group consisting of norepinephrine promoters, selective serotonin receptor agonists, lipase inhibitors, and glucagon-like peptide-1 receptor agonists. Through combined use, it is expected to further improve the efficacy of existing weight imbalance regulators or to reduce the side effects.

In some embodiments of a composition for regulating weight imbalance, preferably, the other weight imbalance regulators are at least one selected from the group consisting of phentermine, bupropion, lorcaserin, orlistat, cetilistat, liraglutide, metformin, zonisamide, topiramate, naltrexone, AMG-598, amitifadine, tesofensine, RZL-12, and other known weight imbalance regulators or compounds having a function of regulating weight imbalance.

In some embodiments of a composition for regulating weight imbalance, the composition is an oral preparation.

The present disclosure has the following beneficial effects:

When used for regulating body weight imbalance, the diosmin hydrogen sulfate having a general structure of formula (I) or a metal salt thereof or a metal complex thereof are unexpectedly discovered to have advantages of high safety, few side effects and excellent efficacy.

DETAILED DESCRIPTION

In order to enable those skilled in the art to better understand the technical solutions and technical effects of the present disclosure after referring to these embodiments, the following exemplary embodiments and their descriptions are provided, but are not used to limit the present disclosure. That is, these embodiments and their descriptions are only exemplary and explanatory, but not restrictive.

Terms

Unless otherwise defined, all technical and scientific terms used herein have the same meaning as commonly understood by those skilled in the art to which the claimed subject matter belongs. When there are multiple definitions of the same term, the definitions in this section shall prevail.

Definitions of standard chemical terms can refer to works such as Advanced Organic Chemistry by Carey and Sundberg, 5th edition, Volume A (2007) and Volume B (2010), Springer.

The term "weight imbalance" mainly refers to overweight or obesity in the present disclosure, that is, a body mass index (BMI) value is equal to or greater than 24. BMI can be calculated from weight and height. BMI=weight (kg)÷(height (m))$^2$ and it is a commonly used standard to measure whether weight is imbalanced. Under normal circumstances, the human BMI has a range of 18.5-24. The larger the value deviates from the normal range, the more serious the weight imbalance. Specifically, 24≤BMI≤28 means overweight and BMI≥28 means obesity. The weight imbalance in the present disclosure is caused by various factors, specifically including diet, drugs, diseases and the like. The weight imbalance in the present disclosure also includes a weight imbalance accompanied by other diseases, such as diabetes, hypertension, hyperlipidemia, hypercholesterolemia, fatty liver, stroke, cerebral thrombosis, heart disease, malignant tumors, hyperuricemia, gout, osteoarthritis, disorders of menstruation, polycystic ovary syndromes or sleep apnea syndrome, etc.

The term "regulating weight imbalance" means the degree of weight imbalance is reduced by regulating or controlling. For example, compared to a BMI value before regulating, the BMI value after regulating is closer to the normal range.

The term "treatment" refers to eradicating, alleviating, reducing or improving diseases or symptoms; for example, delaying development of the diseases or symptoms, reducing the degree of the diseases or symptoms, causing regression of the diseases or symptoms, reducing symptoms caused by the diseases or symptoms, or terminating the diseases or symptoms, etc.

The term "prevention" refers to reducing, lowering or alleviating the risk of specific diseases or symptoms in the future to a certain extent.

The term "effective amount" refers to the amount of at least one drug or compound administered that is sufficient to reduce diseases or symptoms to be regulated, treated, or prevented to a certain extent.

The term "pharmaceutically acceptable excipient" refers to a substance that does not eliminate biological activity of the compound of the present disclosure, and is relatively non-toxic, and can be administered to an individual without causing undesirable biological effects and will not interact with any other components contained in a composition in a harmful way.

The term "pharmaceutical composition" refers to a composition containing an active ingredient. The composition is suitable for direct administration to human body and may or may not include one or more pharmaceutically suitable excipients, including but not limited to vehicles, preservatives, solubilizers, fillers, binders, adsorbents, disintegrants, lubricants, other carriers, other inert ingredients, or combinations thereof.

The term "metal salt" refers to a compound containing a metal element, wherein the metal element part and the other parts of the compound are bonded together mainly through anion and cation interaction.

The term "metal complex" refers to a compound containing a metal element, wherein the metal element part and the other parts of the compound are bonded together mainly through covalent bonds, coordination bonds or intermolecular forces.

The compound of the present disclosure is a diosmin hydrogen sulfate derivative, including a diosmin hydrogen sulfate, a metal salt of the diosmin hydrogen sulfate or a metal complex of the diosmin hydrogen sulfate. In addition, the diosmin hydrogen sulfate derivative also includes its solvates, polymorphs, optical isomers, prodrugs, active metabolites and other derivatives having substantially equivalent pharmacological activity, which are all within the scope of the present disclosure. In formula (I) or formula (II), for the sake of brevity, hydrogen atoms, electric charge identifications and/or chiral center identifications are omitted. Dosmalfate, a specific compound of the present disclosure, is a safe and effective cytoprotective agent with good efficacy on peptic ulcers, and has been used as a drug on the market for many years, for example, dosmalfate tablets with a trade name of "Weiduomei". The mechanism of dosmalfate in treating peptic ulcers may be reducing the activity of pepsin and increasing the concentration of prostaglandin E2. Diosmin is a flavonoid compound, which has good effects of enhancing intravenous tension, improving microcirculation, promoting lymphatic reflux, and reducing edema, achieving good clinical efficacy as a drug for venous diseases. Diosmin has been used as a drug on the market for many years, for example, diosmin tablets with a trade name of "Alvenor".

The pharmaceutical composition of the present disclosure can be prepared by a conventional method in the pharmaceutical field. Standard procedures in the medical field can be used for intervention or treatment of human body.

Example 1 Preparation of Compounds of Present Disclosure

Hydrogen Sulfate of Formula (I)

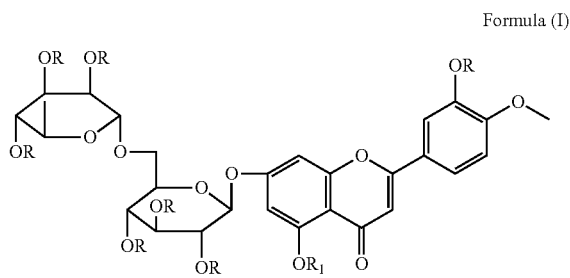

Formula (I)

In formula (I), each R was independently selected from H or —SO$_3$H, R$_1$ was selected from H or —SO$_3$H, and R and R$_1$ were not both H; and preferably, R was —SO$_3$H.

A hydrogen sulfate of formula (I) could be prepared by using diosmin as a raw material, and through a sulfating process. The sulfating agent used in the sulfation process was well known in the art, such as chlorosulfonic acid and the like. There were eight hydroxyl groups in the structure of the raw material diosmin. By controlling reaction conditions, the hydroxyl groups in different positions could be sulfated, and different number of hydroxyl groups could be sulfated, thus obtaining various hydrogen sulfates. For example, a heptahydrogen sulfate was described in patent EP0558435A1 and an octahydrogen sulfate was described in patent EP0302155A1.

Metal Salt of Hydrogen Sulfate

A metal salt of the hydrogen sulfate could be obtained by further alkalizing the hydrogen sulfate. In the alkalization process, a commonly used alkali could be used as an alkalizing agent, such as an alkali containing Na, K, Ca, Al or Mg, so as to form a pharmaceutically applicable metal salt. Different metal salts could be obtained through selecting different alkalizing agents by those skilled in the art, such as sodium salt, potassium salt.

Metal Complex of Hydrogen Sulfate

A metal complex could be obtained by a replacing reaction of the metal salt. The replacement reagent could be an alkali salt, preferably an alkali salt containing hydroxide (or called metal hydroxy salts), so as to obtaining a complex by binding the hydrogen sulfate and a metal hydroxide. An aluminum complex was obtained by treating a sodium salt with an alkaline aluminum chloride as described in Patent EP0558435A1. Different replacement reagents could also be selected by those skilled in the art to obtain different metal complexes.

The following reaction formula listed the concrete preparation process of a heptahydrogen sulfate, an octahydrogen sulfate, a sodium salt and an aluminum complex.

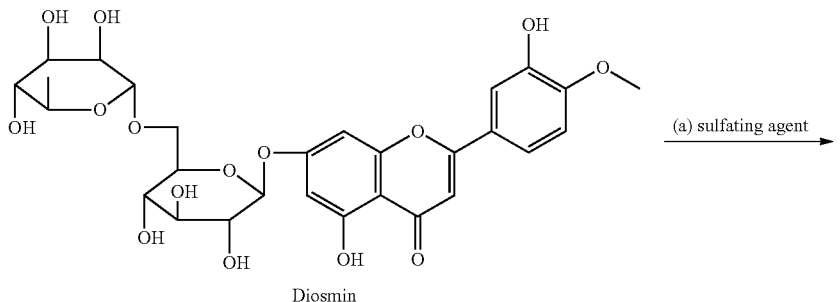

Diosmin

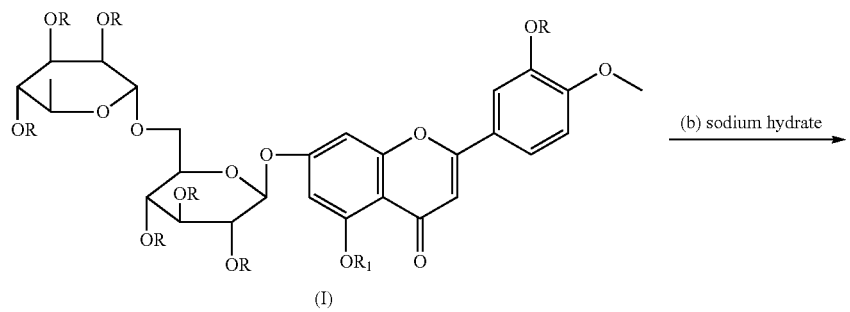

(I)

R = SO$_3$H, R$_1$ = H or SO$_3$H

-continued

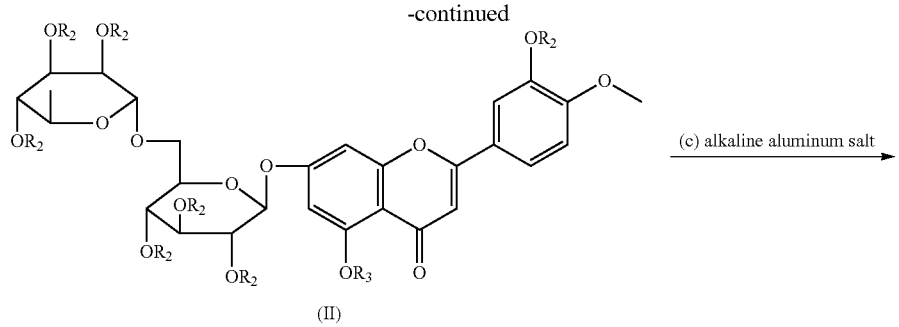

(II)

R = SO$_3$Na, R$_1$ = H or SO$_3$Na

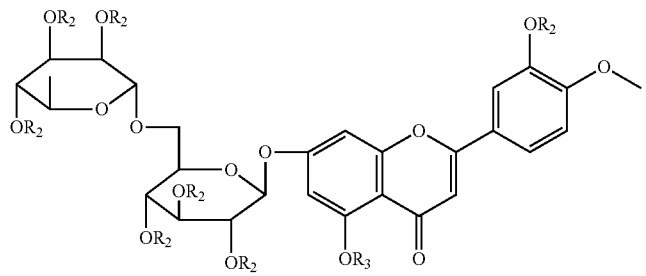

(II)

R = SO$_3$[Al$_2$(OH)$_5$], R$_1$ = H or SO$_3$[Al$_2$(OH)$_5$]

where several representative specific compounds were as follows:

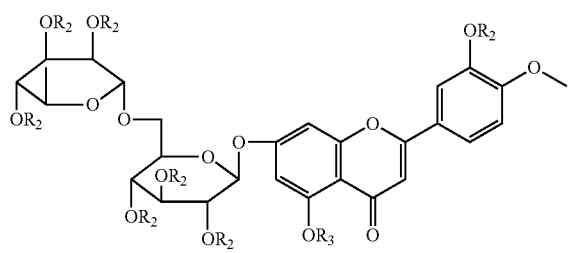

(II)

Compound 1: in a structure of formula (II), R$_2$ was all SO$_3$Na and R$_3$ was H.

Compound 2: in a structure of formula (II), R$_2$ was all SO$_3$Na and R$_3$ was SO$_3$Na.

Compound 3: in a structure of formula (II), R$_2$ was all SO$_3$[Al$_2$(OH)$_5$] and R$_3$ was H.

Compound 4: in a structure of formula (II), R$_2$ was all SO$_3$[Al$_2$(OH)$_5$] and R$_3$ was SO$_3$[Al$_2$(OH)$_5$].

The hydrogen sulfate of formula (I), and the metal salt and the metal complex thereof could also be purchased commercially or prepared according to other existing methods.

Example 2 Clinical Application of Compound of the Present Disclosure

Efficacy and safety of the compound of the present disclosure in treating ulcers were studied in patients suffering from gastric ulcer or duodenal ulcer.

Eighty patients diagnosed with gastric ulcer or duodenal ulcer were treated with tablets of compound 3 (dosmalfate tablets, manufactured by Xiangbei Welman Pharmaceutical Co., LTD.) for 4 weeks. During the treatment, the patients did not take other drugs. The dosage was based on a standard dosage of 3 g per day and should be increased or decreased according to individual conditions of the patients.

Efficacy of Compound of Present Disclosure in Treating Ulcers

The number of ulcer foci and the area of ulcer foci (mm$^2$) of each patient were checked before and after the treatment, and the efficacy after treatment was judged according to the following criteria:

Completely healed: after the treatment, the ulcers and surrounding inflammation all disappeared after an endoscopic examination;

Basically healed: after the treatment, the ulcers disappeared in an endoscopic examination, but there was still inflammation; and partially healed: after the treatment, the area of the ulcers was reduced by 50% or more in an endoscopic examination; and Unhealed: after the treatment, the area of the ulcers was reduced by less than 50% in an endoscopic examination.

The healing rate was used as an indicator of efficacy.

Healing rate=(number of completely healed patients+ number of basically healed patients)÷total number of patients in this group×100%.

Main results were shown in Table 1.

TABLE 1

Healing of peptic ulcers after drug treatment

| Dosage group (g/day) | Number of patients | Healing rate of ulcers |
|---|---|---|
| Group 0.5 g | 10 | 30.0% |
| Group 1 g | 18 | 55.6% |

TABLE 1-continued

Healing of peptic ulcers after drug treatment

| Dosage group (g/day) | Number of patients | Healing rate of ulcers |
|---|---|---|
| Group 3 g | 37 | 62.2% |
| Group 9 g | 10 | 80.0% |
| Group 18 g | 5 | 80.0% |

From the data in Table 1, it could be seen that the compound could effectively promote healing of ulcers.

Safety and Body Weight Regulating Function of Compound of Present Disclosure

The number of red blood cells, the number of white blood cells, ALT, AST, serum creatinine, urine protein and other laboratory test items were checked before and after treatment. Routine clinical diagnostic criterias were used to determine whether the test items were normal and the normal rate was calculated.

Normal rate of test indicators=number of patients with normal test indicators÷total number of patients in this group×100%

Effects of the drug on normal digestive function of the patients were also investigated before and after treatment by determining the rate of loose stool and the rate of constipation:

Rate of loose stool=number of patients with loose stool÷total number of patients in this group× 100%; and Rate of constipation=number of patients with constipation÷total number of patients in this group×100%.

Weight changes of patients before and after treatment were also investigated:

Rate of weight change=(weight after treatment−weight before treatment)÷weight before treatment×100%.

Main results were shown in Table 2.

TABLE 2

Changes of indicators in routine examination before and after drug treatment

| Normal rate of test indicators | Before treatment | After treatment | | | | |
|---|---|---|---|---|---|---|
| | | Group 0.5 g | Group 1 g | Group 3 g | Group 9 g | Group 18 g |
| Normal rate of red blood cells | 92.5% | 100.0% | 94.4% | 94.6% | 90.0% | 80.0% |
| Normal rate of white blood cells | 93.8% | 100.0% | 100.0% | 91.9% | 100.0% | 80.0% |
| Normal rate of ALT | 91.3% | 90.0% | 94.4% | 91.9% | 90.0% | 100.0% |
| Normal rate of AST | 95.0% | 100.0% | 100.0% | 94.6% | 90.0% | 100.0% |
| Normal rate of serum creatinine | 96.3% | 100.0% | 100.0% | 94.6% | 100.0% | 100.0% |
| Normal rate of urine protein | 97.5% | 100.0% | 94.4% | 94.6% | 100.0% | 100.0% |
| Rate of loose stool | 1.3% | 0.0% | 0.0% | 0.0% | 0.0% | 0.0% |
| Rate of constipation | 2.5% | 0.0% | 0.0% | 2.7% | 0.0% | 0.0% |
| Rate of weight change | / | −4.2% | −5.3% | −7.0% | −7.1% | −3.8% |

It could be seen from Table 2 that the compound had good safety, which did not affect the number of red blood cells, the number of white blood cells, ALT, AST, serum creatinine, urine protein and other laboratory test items of the patients basically, and basically had no effect on normal digestive function.

Unexpectedly, a significant effect on weight of the patients was observed by using the compound. Generally, peptic ulcers would lead to less food take and poor digestion of the patients. It has been reported that peptic ulcers could cause weight loss. After the peptic ulcers were relieved, digestive ability of the patients was restored and the weight may increase to varing degrees. However, in the clinical application of dosmalfate tablets, after 4 weeks of administration, patients in each dosage group were unexpectedly found to exhibit weight loss to varing degrees accompanying with relief of ulcers.

Example 3 Function of Compounds of Present Disclosure in Regulating Weight of Obese Model Animals The function of the compounds of the present disclosure in regulating weight was further studied in animal tests.

Test drugs: compound 1, compound 2, compound 3 and compound 4 in Example 1, and sucralfate and diosmin.

Test animals: clean-grade healthy adult male SD rats were selected and randomly grouped into a blank group, a model group, a compound 1 group, a compound 2 group, a compound 3 group, a compound 4 group, a diosmin group and a sucralfate group. Except the blank group and the model group, each group had three subgroups: low dose, middle dose, and high dose. There were 6 animals in each subgroup.

Test Method:

The animals in the blank group were fed with a common feed every day. The animals in each group except the blank group were fed with a formula feed every day. The formula feed contained 5% of cholesterol, 6% of sucrose, 20% of egg yolk, 6% of peanut butter, 12% of whole milk powder, 6% of sesame oil (the percentage was by mass) and other ingredients of the common feed.

Each test drug was mixed with 5% methylcellulose solution; the animals in each group except the blank group and the model group were administered intragastrically respectively with a low dose of 100 mg/kg, a middle dose of 400 mg/kg and a high dose of 1,600 mg/kg; the animals in the blank group and the model group were not administered with the test drug and they were administered intragastrically with the same amount of 5% methylcellulose solution respectively. The intragastric administration was conducted once a day continuously for 4 weeks.

During the test process, the animals in each group were able to eat normally without anorexia. The stool characteristics were normal and no obvious diarrhea occurred.

After the last drug administration, the animals in each group were fasted for 12 h, during which water was provided, and then the animals were weighed.

Body length (distance from the nose to the anus) was measured after the animals were anesthetized with sodium pentobarbital and body mass index (BMI) (BMI=weight (kg)÷(height (m))$^2$) was calculated.

Statistical analysis was conducted by using the data in each group and the main results were screened and shown in Table 3 (Note: some test drugs in the table only list the middle-dose subgroups).

TABLE 3

| Effect of compounds of present disclosure on BMI of rats in obese model | |
|---|---|
| Group | BMI (kg/m$^2$) |
| Blank group | 5.33 ± 0.21* |
| Model group | 7.73 ± 0.27 |
| Low-dose subgroup of compound 3 | 6.72 ± 0.32* |
| Middle-dose subgroup of compound 3 | 6.06 ± 0.29* |
| High-dose subgroup of compound 3 | 5.85 ± 0.23* |
| Middle-dose subgroup of compound 1 | 6.50 ± 0.32* |
| Middle-dose subgroup of compound 2 | 6.63 ± 0.26* |
| Middle-dose subgroup of compound 4 | 6.12 ± 0.35* |
| Middle-dose subgroup of diosmin | 7.60 ± 0.39 |
| Middle-dose subgroup of sucralfate | 7.87 ± 0.34 |

*indicates P < 0.05 compared with the model group.

It could be seen from test results in Table 3:
1) Compared with animals in the blank group, the BMI of animals in the model group increased significantly, indicating that this model was successful;
2) Compared with the model group, after compound 1, compound 2, compound 3 and compound 4 were administrated, the BMI of animals could be significantly reduced, indicating that the compounds had an effect on preventing weight gain. Compound 3 and compound 4 were more effective than compound 1 and compound 2 at the same dose; and
3) There was no significant difference between the sucralfate group or diosmin group and the model group.

Example 4 Regulation of Compound of Present Disclosure in People Suffering from Weight Imbalance Since existing data showed that dosmalfate tablets had good safety, several persons suffering from weight imbalance voluntarily tried tablets of compound 3 (dosmalfate tablets) under a condition of meeting requirements of medical ethics.

Mr. Gao, male, 36 years old, without digestive system or metabolic system diseases, suffering from only mild weight imbalance and having a BMI index of 25. He was administrated with the dosmalfate tablets twice a day (in the morning and in the evening, respectively) with 1 g each time and ate normally. After two months of continuous administration, the BMI index decreased to 22 and body weight returned to a normal level. No adverse reactions related to the dosmalfate tablets occurred during this period.

Ms. Chen, female, 60 years old, suffering from polycystic ovary syndrome, with a weight of 62 kg and a BMI index of 29. After administrated with the dosmalfate tablets three times a day (in the morning, at noon and in the evening, respectively) with 1.5 g each time for three consecutive months. Subsequently, her body weight decreased to 55 kg and the BMI index was 25.7. During the drug administration, only mild constipation was observed without other adverse reactions.

Mr. Sun, male, 64 years old, suffering from obesity and hyperuricemia and having a uric acid level of 680 μmol/L and a weight of 85 kg, with the BMI index up to 32. He was administrated with the dosmalfate tablets three times a day (in the morning, at noon and in the evening, respectively) with 3 g each time for two consecutive months, during which he ate normally. Subsequently, his body weight decreased significantly to 75 kg and the BMI index was 28.2. Although no uric acid-lowering drug was administrated during the drug administration, the uric acid level decreased to 600 μmol/L.

It is indicated from the above data that the compounds of the present disclosure is safe and effective in regulating body weight imbalance.

The above only describes some embodiments of the present disclosure and those skilled in the art should understand that these embodiments are only used to illustrate the present disclosure and not intended to limit the scope of the present disclosure. Those skilled in the art can make changes, substitutions and alterations to the solution of the present disclosure based on the concept of the present disclosure. The protection scope of the present disclosure is defined by the claims, covers their equivalent solutions, and should also cover changes, substitutions and alterations which were made based on the present disclosure by those skilled in the art.

The invention claimed is:

1. A method for weight loss, comprising administering a therapeutically effective amount of a compound to a subject in need thereof, wherein the compound is at least one selected from the group consisting of a hydrogen sulfate having a general structure of formula (I), a metal salt of the hydrogen sulfate having the general structure of formula (I), and a metal complex of the hydrogen sulfate having the general structure of formula (I):

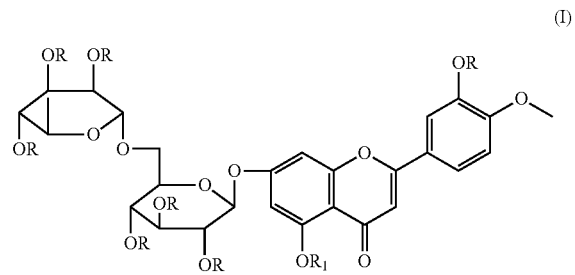

in formula (I),
each R is independently selected from H or —SO$_3$H, R$_1$ is selected from H or —SO$_3$H, and R and R$_1$ are not both H.

2. The method according to claim 1, wherein a metal element in the metal salt or the metal complex is selected from sodium, potassium, calcium, aluminum or magnesium.

3. The method according to claim 1, wherein the metal complex is formed by combining the hydrogen sulfate having the general structure of formula (I) and a metal hydroxide.

4. The method according to claim 1, wherein the compound is selected from a sodium salt, a potassium salt, an aluminum complex, a magnesium complex or a magnesium-aluminum complex of the hydrogen sulfate having the general structure of formula (I).

5. The method according to claim 1, wherein the compound has a structure of formula (II):

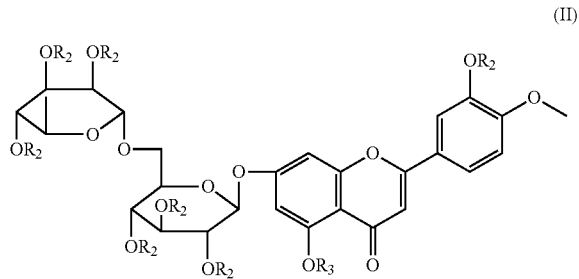

(II)

in formula (II),
R$_2$ is SO$_3$Na and R$_3$ is H; or
R$_2$ is SO$_3$Na and R$_3$ is SO$_3$Na; or
R$_2$ is SO$_3$[Al$_2$(OH)$_5$] and R$_3$ is H; or
R$_2$ is SO$_3$[Al$_2$(OH)$_5$] and R$_3$ is SO$_3$[Al$_2$(OH)$_5$].

6. The method according to claim 1, wherein the compound is orally administered to the subject in need thereof.

7. The method according to claim 1, wherein weight imbalance indicates that the BMI index is not less than 24.

8. The method according to claim 1, further comprising administering an additional weight imbalance regulator to the subject in need thereof, wherein the compound is used as a synergist of the additional weight imbalance regulator.

9. The method according to claim 8, wherein the additional weight imbalance regulator is at least one selected from the group consisting of norepinephrine promoters, selective serotonin receptor agonists, lipase inhibitors, and glucagon-like peptide-1 receptor agonists.

10. The method according to claim 1, wherein an oral dose of the compound is 0.05 g-50 g/day, 0.1 g-30 g/day, 0.5 g-20 g/day, 1 g-18 g/day or 1 g-9 g/day.

11. The method according to claim 5, wherein an oral dose of the compound is 0.05 g-50 g/day, 0.1 g-30 g/day, 0.5 g-20 g/day, 1 g-18 g/day or 1 g-9 g/day.

12. The method according to claim 6, wherein the compound is administrated orally 1-3 times/day.

13. The method according to claim 1, wherein the method is for therapeutic or non-therapeutic purposes.

14. The method according to claim 1, wherein R is —SO$_3$H.

15. The method according to claim 8, wherein the weight imbalance regulator is at least one selected from the group consisting of phentermine, bupropion, lorcaserin, orlistat, cetilistat, liraglutide, metformin, zonisamide, topiramate, naltrexone, AMG-598, amitifadine, tesofensine, and tapencarium.

* * * * *

UNITED STATES PATENT AND TRADEMARK OFFICE
CERTIFICATE OF CORRECTION

PATENT NO. : 12,274,710 B2
APPLICATION NO. : 17/608203
DATED : April 15, 2025
INVENTOR(S) : Tianyu Sun et al.

Page 1 of 1

It is certified that error appears in the above-identified patent and that said Letters Patent is hereby corrected as shown below:

On the Title Page

Item (73) the FOURTH ASSIGNEE should be CORRECTED as follows:
GUANGZHOU WELMAN NEW DRUG R&D CO., LTD., GUANGZHOU (CN)

Item (73) should be corrected to ADD the FIFTH ASSIGNEE as follows:

NANJING KANGFUSHUN PHARMACEUTICAL CO., LTD, NANJING, JIANGSU (CN)

Signed and Sealed this
Fifteenth Day of July, 2025

Coke Morgan Stewart
*Acting Director of the United States Patent and Trademark Office*